United States Patent

Gamblin et al.

[11] Patent Number: 5,674,809
[45] Date of Patent: Oct. 7, 1997

[54] HERBICIDAL MIXTURES COMPRISING DIFLUFENICAN AND A SUBSTITUTED 3-PHENYLPYRAZOLE

[75] Inventors: Alan Gamblin, Essex, England; Jacques Rognon, Lyons, France

[73] Assignee: Rhone-Poulenc Agrochimie, Lyons Cedex, France

[21] Appl. No.: 580,209

[22] Filed: Dec. 28, 1995

Related U.S. Application Data

[62] Division of Ser. No. 246,287, May 19, 1994, Pat. No. 5,502,026.

[30] Foreign Application Priority Data

May 19, 1993 [FR] France ................................. 93 06271

[51] Int. Cl.⁶ ........................... A01N 43/40; A01N 43/56
[52] U.S. Cl. ...................................... 504/130; 504/138
[58] Field of Search ................................ 504/139, 130

[56] References Cited

U.S. PATENT DOCUMENTS 3,935,000  1/1976  Fischer ........................... 71/91

FOREIGN PATENT DOCUMENTS

| 0273669 | 7/1988 | European Pat. Off. . |
| 0443059 | 8/1991 | European Pat. Off. . |
| 0531116 | 3/1993 | European Pat. Off. . |
| 2671457 | 7/1992 | France . |
| 2701195 | 8/1994 | France . |
| 2341594 | 2/1975 | Germany . |
| 2274780 | 8/1994 | United Kingdom . |

OTHER PUBLICATIONS

*Chemical Abstracts*, vol. 117, No. 5, Aug. 3, 1992, abstract No. 42744k.
English translation of JP 04–059706 published Feb. 26, 1992.
*Chemical Abstracts*, vol. 116, No. 11, Mar. 16, 1992, abstract No. 101131n.
English translation of JP 03–246204 published Nov. 1, 1991.
Database Chemabs, CA 109(19):165724w (1988), abstract of JP 63–079804, published Apr. 9, 1988.
Database WPI/Derwent, AN–88–137242 (1988), abstract of JP 63–079804, published Apr. 9, 1988.
Database PAJ/JPO, abstract of JP63–079804 published Apr. 9, 1988.
*The Agrochemicals Handbook*, "Aclonifen", Bromoxynil, Diflufenican, Isoproturon, 1987.
*Chemical Abstracts*, 115:177436 (abstract of South African Appln. No. 9000663, published Oct. 31, 1990).
Derwent WPI, 91–037005 (abstract of South African Appln. No. 900000663, published Oct. 31, 1990).
*Chemical Abstracts*, 111:189596 (abstract of JP 01121203, published May 12, 1989).
Derwent WPI, 89–182749 (abstract of JP 01121203, published May 12, 1989).

*Primary Examiner*—S. Mark Clardy
*Attorney, Agent, or Firm*—Burns, Doane, Swecker & Mathis, L.L.P.

[57] ABSTRACT

Herbicidal compositions, characterized in that they comprise: (a) as active ingredient, a herbicidally effective amount of a mixture comprising HERB1, known under the chemical name of 1-methyl-3-[2-fluoro-4-chloro-5-(ethoxycarbonylmethoxy)phenyl]-4-chloro-5-difluoromethoxypyrazole (I), and a second herbicide (II) selected from the group consisting of diflufenican, bromoxynil, flurtamone, aclonifen and isoproturon; and (b) an agriculturally acceptable carrier therefor.

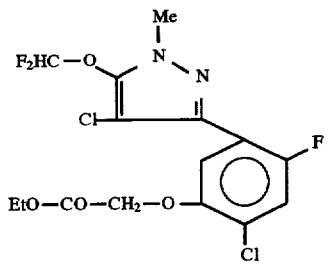

21 Claims, No Drawings

HERBICIDAL MIXTURES COMPRISING DIFLUFENICAN AND A SUBSTITUTED 3-PHENYLPYRAZOLE

This application is a divisional of application Ser. No. 08/246,287, filed May 19, 1994 now U.S. Pat. No. 5,502,026.

BACKGROUND OF THE INVENTION

1. Field of the Invention

The present invention relates to herbicidal mixtures and to herbicidal compositions comprising them which have improved performance, and to their use in treating crops.

2. Description of the Prior Art

The herbicide termed hereinbelow HERB1, whose chemical name is 1-$CH_3$-3-[2-F-4-Cl-5-(—O—$CH_2$—CO—O—$C_2H_5$)phenyl]-4-Cl-5-$OCHF_2$-pyrazole, i.e., 1-methyl-3-[2-fluoro-4-chloro-5-(ethoxycarbonylmethoxy)phenyl]-4-chloro-5-difluoromethoxypyrazole, is known. This compound is described in European patent applications published under numbers 0361114 and 0043059. This herbicide is known essentially for its use in growing paddy rice or upland rice and in locations where no selectivity is required, such as swamps, orchards, mountain regions and verges. This herbicide is also known as being particularly active even at very low doses in such a way that its effectiveness is quite considerable at low dosage rates and that the results of combination with other herbicides are quite unpredictable. Moreover, the above-cited European patent publications do not suggest any particular herbicidal mixture.

SUMMARY OF THE INVENTION

It has now been found that mixtures of HERB1 with certain specific herbicides provide high-performance herbicidal compositions which are selective with regard to cereals. Other advantages of the present invention will become apparent from the description which follows, in particular the good activity of the mixtures and compositions according to the invention on weeds in cereals, especially weeds which are a serious economic problem.

More precisely, the invention relates to herbicidal mixtures comprising HERB1 (I) and a second herbicide (II) selected from the group consisting of diflufenican, bromoxynil, flurtamone, aclonifen and isoproturon; and to herbicidal compositions comprising: (a) as active ingredient, a herbicidally effective amount of a mixture comprising HERB1 (I) and a second herbicide (II) selected from the group consisting of diflufenican, bromoxynil, flurtamone, aclonifen and isoproturon; and (b) an agriculturally acceptable carrier therefor.

In another aspect, the present invention provides herbicidal mixtures consisting of HERB1 (I) and at least one further herbicide (II) selected from the group consisting of diflufenican, bromoxynil, flurtamone, aclonifen and isoproturon; and herbicidal compositions comprising: (a) as active ingredient, a herbicidally effective amount of a mixture consisting of HERB1 (I) and at least one further herbicide (II) selected from the group consisting of diflufenican, bromoxynil, flurtamone, aclonifen and isoproturon; and (b) an agriculturally acceptable carrier therefor.

In still another aspect, the invention provides herbicidal mixtures comprising a synergistic amount of HERB1 (I) and a second herbicide (II) selected from the group consisting of diflufenican, bromoxynil, flurtamone, aclonifen and isoproturon; and herbicidal compositions comprising: (a) as active ingredient, a synergistic herbicidally effective amount of a mixture comprising HERB1 (I) and a second herbicide (II) selected from the group consisting of diflufenican, bromoxynil, flurtamone, aclonifen and isoproturon; and (b) an agriculturally acceptable carrier therefor.

Yet another aspect of the present invention provides herbicidal mixtures consisting of a synergistic amount of HERB1 (I) and at least one further herbicide (II) selected from the group consisting of diflufenican, bromoxynil, flurtamone, aclonifen and isoproturon; and herbicidal compositions comprising: (a) as active ingredient, a synergistic herbicidally effective amount of a mixture consisting of HERB1 (I) and at least one further herbicide (II) selected from the group consisting of diflufenican, bromoxynil, flurtamone, aclonifen and isoproturon; and (b) an agriculturally acceptable carrier therefor.

In yet other aspects of the invention, there are provided methods for protecting crops against weeds and/or improving crop yields by applying the mixtures and compositions described above.

DETAILED DESCRIPTION OF THE INVENTION AND THE PREFERRED EMBODIMENTS

More particularly according to the present invention, the second herbicide (II) is identified as follows:

Diflufenican is the compound having the chemical name N-(2,4-difluorophenyl)-2-[3-(trifluoromethyl)phenoxy]pyridinecarboxamide.

Bromoxynil is 2,6-dibromo-4-cyanophenol. It can be used in phenol form or, preferably, in the form of salts, or, more preferably, in ester form, especially in the form of an alkanoate derived from an alkanoic acid having not more than 10 carbon atoms, for example, the octanoate ester.

Flurtamone is the compound having the chemical name 2-methylamino-3-(4-trifluoromethylphenyl)-4-oxo-5-phenyl-4,5-dihydrofuran.

Aclonifen is the compound having the chemical name 2-chloro-6-nitro-3-phenoxyaniline.

Isoproturon is the compound having the chemical name N,N-dimethyl-N'-(4-isopropylphenyl)urea.

The ratio by weight of compound (I) to compound (II) in the mixtures and compositions according to the invention is generally as follows:

between about 0.5 and 0.04, preferably between about 0.06 and 0.3, in the case of the mixture of (I) with diflufenican;

between about 0.005 and 0.5, preferably between about 0.02 and 0.2, in the case of the mixture of (I) with bromoxynil;

between about 0.005 and 0.5, preferably between about 0.01 and 0.1, in the case of the mixture of (I) with flurtamone;

between about 0.005 and 0.5, preferably between about 0.01 and 0.2, in the case of the mixture of (I) with aclonifen;

between about 0.001 and 0.5, preferably between about 0.002 and 0.02, in the case of the mixture of (I) with isoproturon.

As a general rule, the herbicidal compositions according to the invention contain from about 0.5 to about 95% of active ingredient [i.e., of mixture of (I) and (II)].

The compositions of the invention can be made at the time of use, or diluted, or else they can be concentrated compositions, or so-called "ready-to-use" compositions, that is to say, ready for marketing.

The compositions according to the invention can, moreover, comprise any additives or adjuvants conventionally used in crop protection products, in particular carriers, surfactants, adhesives and dispersants.

The compositions according to the invention can be in solid or liquid form, and in the form of solutions, suspensions, emulsions or emulsifiable concentrates.

The term "carrier" is to be understood as meaning, in the present text, an organic or inorganic natural or synthetic substance with which the active ingredients are combined to aid their application to the plant, the seeds or the soil. This carrier is therefore generally inert and must be agriculturally acceptable, in particular for the treated plant. The carrier can be solid (for example, clays, natural or synthetic silicates, silica, resins, waxes, solid fertilizers and the like) or liquid (for example, water, alcohols, ketones, petroleum fractions, aromatic or paraffinic hydrocarbons, chlorinated hydrocarbons, liquefied gases and the like).

The surfactant can be an emulsifier, dispersant or wetting agent of ionic or non-ionic nature. Examples which may be mentioned are salts of polyacrylic acids, salts of lignosulfonic acids, salts of phenolsulfonic or naphthalenesulfonic acids, polycondensates of ethylene oxide with fatty alcohols or with fatty acids or with fatty amines, substituted phenols (in particular alkylphenols or arylphenols), salts of sulfosuccinates, murine derivatives (in particular alkyltaurates), and phosphoric esters of alcohols or of polyoxyethylated phenols. It is desirable for at least one surfactant to be present so as to favor dispersion of the active ingredients in water and their correct application to the plants.

These compositions can also contain all manner of other ingredients, such as, for example, protective colloids, adhesives, thickeners, thixotropic agents, penetrants, stabilizers, sequestering agents, pigments, colorants and polymers.

More generally speaking, the compositions according to the invention can include any solid or liquid additives which are conventionally used in the art of formulation of herbicidal compositions.

Among the compositions, the following may be mentioned generally: solid or liquid compositions, but liquid compositions are preferred, for their convenience of use as well as their simple preparation.

As solid forms of compositions, the following may be mentioned: powders for dusting or dispersing (with an active compound content of up to 100%) and granules, in particular those obtained by extrusion, compacting, impregnation of a granulated carrier, or granulation of a powder (the active compound content in these granules being between about 1 and 80% in the latter cases).

As liquid forms of compositions, or forms of compositions which are intended to constitute liquid compositions on application, the following may be mentioned: solutions, in particular water-soluble concentrates, emulsifiable concentrates, emulsions, concentrated suspensions, aerosols, wettable powders (or sprayable powders) and pastes.

The emulsifiable or soluble concentrates comprise most frequently from about 10 to 80% of active ingredients, and the ready-to-use emulsions or solutions contain, for their part, from about 0.01 to 20% of active ingredients.

In addition to the solvent, the emulsifiable concentrates can contain, if necessary, from about 2 to 20% of suitable additives, such an stabilizers, surfactants, penetrants, corrosion inhibitors, colorants or the above-mentioned adhesives.

Using these concentrates, emulsions of any desired concentration which are particularly suitable for foliar application, can be obtained by dilution with water.

The concentrated suspensions, which can also be applied by spraying, are prepared in such a manner that a stable fluid product is obtained which does not form sediments; these generally contain from about 10 to 75% of active ingredients, from about 0.5 to 15% of surfactants, from about 0.1 to 10% of thixotropic agents, from about 0 to 10% of suitable additives, such as pigments, colorants, antifoams, corrosion inhibitors, stabilizers, penetrants and adhesives, and, as a carrier, water or an organic liquid in which the active ingredients are sparingly soluble or insoluble. Certain solid organic substances or mineral salts can be dissolved in the carrier to help prevent the formation of sediments or as antifreeze agents for the water.

The wettable powders (or sprayable powders) are generally prepared in such a manner that they contain from about 20 to 95% of active ingredients, and they generally contain, in addition to the solid carrier, from about 0 to 5% of a wetting agent, from about 3 to 10% of a dispersant and, if necessary, from about 0 to 10% of one or more stabilizers and/or other additives, such as pigments, colorants, penetrants, adhesives, anticaking agents and the like.

To obtain these sprayable powders or wettable powders, the active ingredients are intimately mixed with the additional substances in suitable mixers, and the mixtures are ground in suitable mills or other grinders. In this way, sprayable powders with advantageous wettability and suspensibility are obtained; they can be suspended in water at any desired concentration, and these suspensions can be used in a highly advantageous manner in particular for application to the leaves of plants.

Instead of wettable powders, pastes can be prepared. The conditions and circumstances of making and using these pastes are similar to those for the wettable powders or sprayable powders.

The dispersible granules are generally prepared by agglomeration in suitable granulation systems of a composition of the wettable powder type.

As has already been said, the aqueous dispersions and emulsions, for example the compositions obtained by diluting a wettable powder or an emulsifiable concentrate according to the invention with water are part of the general scope of the present invention. The emulsions can be of the water-in-oil or oil-in-water type and they can have a thick consistency, such as the consistency of mayonnaise.

Among these compositions, the expert will advantageously choose that or those which is/are suitable for the chosen combinations.

In most cases, the compositions can contain two growth regulator herbicides as defined hereinabove (binary combination) or three (three-way combination) or even four (four-way combination).

The invention also relates to a process for treating crops in order to protect these crops against weeds and/or to improve crop yields, comprising applying an effective and non-phytotoxic dose of a mixture or composition according to the invention to the leaves of the plants.

In accord with the process of the invention, herbicidal compositions which comprise the active ingredients (I) and (II) which have been defined hereinabove are applied to the surface to be treated, that is to say to the surface (locus)

which is infested, or susceptible to being infested, with weeds, in particular weeds which are noxious to cereals, these active ingredients being applied at a dose of from about 3 to 25 g/ha in the case of active ingredient (I) (that is to say, herbicide HERB1), preferably of from about 5 to 15 g/ha, and at the dose of:

from about 30 to 150 g/ha, preferably between about 50 and 100 g/ha, in the case of diflufenican;

from about 100 to 300 g/ha, preferably between about 150 and 250 g/ha, in the case of bromoxynil;

from about 200 to 400 g/ha, preferably between about 250 and 375 g/ha, in the case of flurtamone;

from about 100 to 300 g/ha, preferably between about 150 and 250 g/ha, in the case of aclonifen;

from about 800 to 2000 g/ha, preferably between about 1200 and 1500 g/ha, in the case of isoproturon.

Among the crops to which the mixtures and preferably the compositions according to the invention can be applied, the cereals are those mainly of interest, in particular wheat, barley, oats, rye and their hybrids; the bromoxynil-based mixture is, moreover, particularly suitable for weed control in maize. In addition to good selectivity exhibited by the mixtures/compositions according to the invention with regard to cereals, the mixtures/compositions have, moreover, good activity for crops which are infested, or susceptible to being infested, with cleavers (*Galium aparine*). This weed is a problem which is particularly difficult to solve because very few herbicidal products destroy it with a high degree of effectiveness. Thus, two plants per square meter are enough to reduce the yield of the cereals. Veronica (*Veronica hederifolia*) is another problem which is difficult to solve because it is a weed which emerges very early in the autumn, emerges very quickly and develops even during winter in such a way that destroying it cannot be postponed until spring.

The process of the invention can be carried out by using a ready-to-use composition or by mixing the different active ingredients at the time of use just before they are employed (tank mix). The composition can also be formed in situ by successive foliar applications of the different active ingredients.

The following examples, which are not given by of limitation, illustrate the invention and show how it can be carried out. In the case of certain weeds, these examples show a particularly significant effect. These examples correspond to selected cases of weeds which are difficult to control.

EXAMPLE 1

Plots of winter wheat and winter barley, which also contained different weeds, were treated. Treatment was carried out in autumn after emergence of the crop and of the weeds.

The herbicidal composition was obtained by mixing a concentrated suspension of HERB1 and a concentrated suspension of aclonifen in the tank for dilution with water at the time of use.

The treatment was carried out by way of comparison with two treatments, which employed each of the two herbicides at its correct dose as employed in the mixture.

At the end of winter, the following destruction rates, which are expressed as a percentage, were observed:

| Active ingredient | (I) alone | Aclonifen alone | Mixture |
| --- | --- | --- | --- |
| Dose of active ingredient(s) in g/ha | 6 | 200 | 6 + 200 |
| Destruction rate of cleavers (*Galium aparine*) in percent | 65 | 0 | 100 |

| Active ingredient | (I) alone | Aclonifen alone | Mixture |
| --- | --- | --- | --- |
| Dose of active ingredient(s) in g/ha | 9 | 200 | 9 + 200 |
| Destruction rate of cleavers (*Galium aparine*) in percent | 95 | 0 | 100 |

The mixture was completely selective, i.e., no crop damage was caused in wheat and barley.

EXAMPLE 2

The process was carried out as in EXAMPLE 1, but bromoxynil octanoate was used instead of aclonifen.

At the end of winter, the following destruction rates, which are expressed as a percentage, were observed:

| Active ingredient | (1) alone | Bromoxynil ester | Mixture |
| --- | --- | --- | --- |
| Dose of active ingredient(s) in g/ha | 6 | 200 | 6 + 200 |
| Destruction rate of cleavers (*Galium aparine*) in percent | 65 | 0 | 100 |
| Destruction rate of field pansy (*Viola arvensis*) in percent | 0 | 0 | 95 |

The mixture was completely selective, i.e., there was no crop damage caused, in wheat and barley.

EXAMPLE 3

The process was carried out as in EXAMPLE 1, but isoproturon was used instead of aclonifen.

At the end of winter, the following destruction rates, which are expressed as a percentage, were observed:

| Active ingredient | (I) alone | Isoproturon | Mixture |
| --- | --- | --- | --- |
| Dose of active ingredient(s) in g/ha | 6 | 1500 | 6 + 1500 |
| Destruction rate of veronica (*Veronica hederifolia*) in percent | 60 | 0 | 80 |

The mixture was completely selective, i.e., no crop damage was caused, in wheat and barley. Seventy percent of the cleavers (*Galium aparine*) were destroyed.

EXAMPLE 4

The process was carried out as in EXAMPLE 1, but flurtamone was used instead of aclonifen.

At the end of winter, the following destruction rates, which are expressed as a percentage, were observed:

| Active ingredient | (I) alone | Flurtamone | Mixture |
|---|---|---|---|
| Dose of active ingredient(s) in g/ha | 6 | 325 | 6 + 325 |
| Destruction rate of cleavers (*Galium aparine*) in percent | 65 | 60 | 100 |
| Destruction rate of Italian rye grass (*Lolium multiflorum*) in percent | 0 | 85 | 95 |
| Destruction rate of field pansy (*Viola arvensis*) in percent | 0 | 60 | 70 |

The mixture was completely selective, i.e., there was no crop damage caused, in wheat and barley.

EXAMPLE 5

The process was carried out as in EXAMPLE 1, but diflufenican was used instead of aclonifen.

At the end of winter, the following destruction rates, which are expressed as a percentage, were observed:

| Active ingredient | (I) alone | Diflufenican | Mixture |
|---|---|---|---|
| Dose of active ingredient(s) in g/ha | 6 | 50 | 6 + 50 |
| Destruction rate of cleavers (*Galium aparine*) in percent | 65 | 65 | 95 |

At the end of winter, a 98% destruction of cleavers and the following other results were observed:

| Active ingredient | (I) alone | Diflufenican | Mixture |
|---|---|---|---|
| Dose of active ingredient(s) in g/ha | 6 | 50 | 6 + 50 |
| Destruction rate of chamomile (*Matricaria inodora*) in percent | 51 | 33 | 95 |
| Destruction rate of poppy (*Papaver rhosas*) in percent | 45 | 60 | 96 |

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A herbicidal mixture comprising a synergistic herbicidally effective amount of 1-methyl-3-[2-fluoro-4-chloro-5-ethoxycarbonylmethoxy)phenyl]-4-chloro-5-difluoromethoxypyrazole (I) and diflufenican (II).

2. A herbicidal mixture according to claim 1, wherein the ratio by weight of (I) to (II) is between about 0.04 and about 0.5.

3. A herbicidal mixture according to claim 2, wherein the ratio by weight of (I) to (II) is between about 0.06 and about 0.3.

4. A herbicidal mixture consisting essentially of a synergistic herbicidally effective amount of 1-methyl-3-[2-fluoro-4-chloro-5-(ethoxycarbonylmethoxy)phenyl]-4-chloro-5-difluoromethoxypyrazole (I) and diflufenican (II).

5. A herbicidal mixture according to claim 4, wherein the ratio by weight of (I) to (II) is between about 0.04 and about 0.5.

6. A herbicidal mixture according to claim 5, wherein the ratio by weight of (I) to (II) is between about 0.06 and about 0.3.

7. A herbicidal composition comprising:

(a) a synergistic herbicidally effective amount of a mixture comprising 1-methyl-3-[2-fluoro-4-chloro-5-(ethoxycarbonylmethoxy)phenyl]-4-chloro-5-difluoromethoxypyrazole (I) and diflufenican (II); and (b) an agriculturally acceptable carrier therefor.

8. A herbicidal composition according to claim 7, wherein the ratio by weight of (I) to (II) is between about 0.04 and about 0.5.

9. A herbicidal composition according to claim 8, wherein the ratio by weight of (I) to (II) is between about 0.06 and about 0.3.

10. A herbicidal composition according to claim 7, comprising from about 0.5 to about 95% of active ingredients (I) and (II).

11. A herbicidal composition comprising:

(a) a synergistic herbicidally effective amount of a mixture consisting essentially of 1-methyl-3-[2-fluoro-4-chloro-5-(ethoxycarbonylmethoxy)phenyl]-4-chloro-5-difluoromethoxypyrazole (I) and diflufenican (II); and (b) an agriculturally acceptable carrier therefor.

12. A herbicidal composition according to claim 11, wherein the ratio by weight of (I) to (II) is between about 0.04 and about 0.5.

13. A herbicidal composition according to claim 12, wherein the ratio by weight of (I) to (II) is between about 0.06 and about 0.3.

14. A method for protecting a crop against weeds and/or for improving crop yields, said method comprising applying to the leaves of the plants or to the locus in which they grow, a synergistic herbicidally effective, non-phytotoxic amount of a mixture as claimed in claim 1.

15. A method according to claim 14, wherein (I) is applied at a rate of from about 3 to about 15 g/ha and (II) is applied at a rate of from about 30 to about 150 g/ha.

16. A method according to claim 15, wherein (I) is applied at a rate of from about 5 to about 10 g/ha and (II) is applied at a rate of from about 50 to about 100 g/ha.

17. A method according to claim 14, wherein the crop is a wheat, barley, oat or rye crop.

18. A method for protecting a crop against weeds and/or for improving crop yields, said method comprising applying to the leaves of the plants or to the locus in which they grow, a synergistic herbicidally effective, non-phytotoxic amount of a composition as claimed in claim 7.

19. A method according to claim 18, wherein (I) is applied at a rate of from about 3 to about 15 g/ha and (II) is applied at a rate of from about 30 to about 150 g/ha.

20. A method according to claim 19, wherein (I) is applied at a rate of from about 5 to about 10 g/ha and (II) is applied at a rate of from about 50 to about 100 g/ha.

21. A method according to claim 18, wherein the crop is a wheat, barley, oat or rye crop.

* * * * *